US010068749B2

(12) United States Patent
Fuller et al.

(10) Patent No.: US 10,068,749 B2
(45) Date of Patent: Sep. 4, 2018

(54) PREPARATION OF LAMELLAE FOR TEM VIEWING

(71) Applicants: Scott Edward Fuller, Portland, OR (US); Brian Roberts Routh, Jr., Beaverton, OR (US); Michael Moriarty, Portland, OR (US)

(72) Inventors: Scott Edward Fuller, Portland, OR (US); Brian Roberts Routh, Jr., Beaverton, OR (US); Michael Moriarty, Portland, OR (US)

(73) Assignee: FEI Company, Hillsboro, OR (US)

( * ) Notice: Subject to any disclaimer, the term of this patent is extended or adjusted under 35 U.S.C. 154(b) by 263 days.

(21) Appl. No.: 13/899,278

(22) Filed: May 21, 2013

(65) Prior Publication Data
US 2013/0319849 A1 Dec. 5, 2013

Related U.S. Application Data

(60) Provisional application No. 61/649,917, filed on May 21, 2012.

(51) Int. Cl.
C23C 14/00 (2006.01)
C23C 14/32 (2006.01)
(Continued)

(52) U.S. Cl.
CPC ............ H01J 37/3026 (2013.01); G01N 1/32 (2013.01); H01J 2237/31745 (2013.01)

(58) Field of Classification Search
CPC ....................................................... G01N 1/32
See application file for complete search history.

(56) References Cited

U.S. PATENT DOCUMENTS 4,620,898 A 11/1986 Banks et al.
5,435,850 A 7/1995 Rasmussen
(Continued)

FOREIGN PATENT DOCUMENTS

JP H07333120 A 12/1995
JP H11223588 A 8/1999
(Continued)

OTHER PUBLICATIONS

Hähnel, A., Reiche, M., Moutanabbir, O., Blumtritt, H., Geisler, H., Hoentschel, J. and Engelmann, H.-J. (2011), Nano-beam electron diffraction evaluation of strain behaviour in nano-scale patterned strained silicon-on-insulator. Phys. Status Solidi C, 8: 1319-1324. doi: 10.1002/pssc.201084007.*

(Continued)

Primary Examiner — Ibrahime A Abraham
(74) Attorney, Agent, or Firm — Scheinberg & Associates, P.C.; John B. Kelly

(57) ABSTRACT

A method and apparatus for producing thin lamella for TEM observation. The steps of the method are robust and can be used to produce lamella in an automated process. In some embodiments, a protective coating have a sputtering rate matched to the sputtering rate of the work piece is deposited before forming the lamella. In some embodiments, the bottom of the lamella slopes away from the feature of interest, which keeps the lamella stable and reduces movement during thinning. In some embodiments, a fiducial is used to position the beam for the final thinning, instead of using an edge of the lamella. In some embodiments, the tabs are completed after high ion energy final thinning to keep the lamella more stable. In some embodiments, a defocused low ion energy and pattern refresh delay is used for the final cut to reduce deformation of the lamella.

20 Claims, 16 Drawing Sheets

(51) Int. Cl.
*H01J 37/302* (2006.01)
*G01N 1/32* (2006.01)

(56) References Cited

U.S. PATENT DOCUMENTS

| | | | |
|---|---|---|---|
| 5,851,413 A | 12/1998 | Casella et al. | |
| 6,080,991 A * | 6/2000 | Tsai | G01N 1/286 250/492.21 |
| 6,194,720 B1 | 2/2001 | Li et al. | |
| 6,570,170 B2 | 5/2003 | Moore | |
| 6,794,720 B2 | 9/2004 | Yagishita et al. | |
| 7,473,496 B2 | 1/2009 | Cheng | |
| 7,880,151 B2 | 2/2011 | Wells | |
| 8,134,124 B2 | 3/2012 | Blackwood et al. | |
| 8,357,913 B2 | 1/2013 | Agorio et al. | |
| 8,455,821 B2 | 6/2013 | Arjavac et al. | |
| 2005/0037625 A1 | 2/2005 | Anciso et al. | |
| 2007/0158566 A1 | 7/2007 | Ikeda | |
| 2009/0218488 A1* | 9/2009 | Wells | 250/307 |
| 2010/0276607 A1* | 11/2010 | Wanzenboeck et al. | 250/440.11 |
| 2010/0300873 A1* | 12/2010 | Blackwood et al. | 204/192.33 |
| 2010/0308219 A1 | 12/2010 | Blackwood et al. | |
| 2012/0152731 A1 | 6/2012 | Blackwood et al. | |
| 2013/0153785 A1 | 6/2013 | Agorio et al. | |

FOREIGN PATENT DOCUMENTS

| | | |
|---|---|---|
| JP | 2001-021467 | 1/2001 |
| JP | 2002228562 A | 8/2002 |
| JP | 2008177154 A | 7/2008 |
| JP | 2010507783 | 3/2010 |
| JP | 2011185845 | 9/2011 |
| JP | 2011221023 | 11/2011 |
| JP | 2012012704 A | 1/2012 |
| KR | 10-2005-0033699 | 4/2005 |
| WO | 2012005232 A1 | 1/2012 |

OTHER PUBLICATIONS

Unknown, "Through Silicon Via (TSV) Wafer Finishing & Flip Chip Stacking," retrieved May 17, 2012, 2 pgs.

Michael Moriarty, et al,. "Repeatability of Automated FIB Prepared TEM Samples with Low keV Cleaning", Jul. 2010, pp. 204-205, vol. 16, Supp. S2.

* cited by examiner

PREPARATION OF LAMELLAE FOR TEM VIEWING

This Application claims priority from U.S. Provisional Application 61/649,917, filed May 21, 2012, which is hereby incorporated by reference.

TECHNICAL FIELD OF THE INVENTION

The invention relates to the automated preparation of sample for viewing on a transmission electron microscope.

BACKGROUND OF THE INVENTION

Semiconductor manufacturing, such as the fabrication of integrated circuits, typically entails the use of photolithography. A semiconductor substrate on which circuits are being formed, usually a silicon wafer, is coated with a material, such as a photoresist, that changes solubility when exposed to radiation. A lithography tool, such as a mask or reticle, positioned between the radiation source and the semiconductor substrate casts a shadow to control which areas of the substrate are exposed to the radiation. After the exposure, the photoresist is removed from either the exposed or the unexposed areas, leaving a patterned layer of photoresist on the wafer that protects parts of the wafer during a subsequent etching or diffusion process.

The photolithography process allows multiple integrated circuit devices or electromechanical devices, often referred to as "chips," to be formed on each wafer. The wafer is then cut up into individual dies, each including a single integrated circuit device or electromechanical device. Ultimately, these dies are subjected to additional operations and packaged into individual integrated circuit chips or electromechanical devices.

During the manufacturing process, variations in exposure and focus require that the patterns developed by lithographic processes be continually monitored or measured to determine if the dimensions of the patterns are within acceptable ranges. The importance of such monitoring, often referred to as process control, increases considerably as pattern sizes become smaller, especially as minimum feature sizes approach the limits of resolution available by the lithographic process. In order to achieve ever-higher device density, smaller and smaller feature sizes are required. This may include the width and spacing of interconnecting lines, spacing and diameter of contact holes, and the surface geometry such as corners and edges of various features. Features on the wafer are three-dimensional structures and a complete characterization must describe not just a surface dimension, such as the top width of a line or trench, but a complete three-dimensional profile of the feature. Process engineers must be able to accurately measure the critical dimensions (CD) of such surface features to fine tune the fabrication process and assure a desired device geometry is obtained.

Typically, CD measurements are made using instruments such as a scanning electron microscope (SEM). In a scanning electron microscope (SEM), a primary electron beam is focused to a fine spot that scans the surface to be observed. Secondary electrons are emitted from the surface as it is impacted by the primary beam. The secondary electrons are detected, and an image is formed, with the brightness at each point of the image being determined by the number of secondary electrons detected when the beam impacts a corresponding spot on the surface. As features continue to get smaller and smaller, however, there comes a point where the features to be measured are too small for the resolution provided by an ordinary SEM.

Transmission electron microscopes (TEMs) allow observers to see extremely small features, on the order of nanometers. In contrast SEMs, which only image the surface of a material, TEM also allows analysis of the internal structure of a sample. In a TEM, a broad beam impacts the sample and electrons that are transmitted through the sample are focused to form an image of the sample. The sample must be sufficiently thin to allow many of the electrons in the primary beam to travel though the sample and exit on the opposite site. Samples, also referred to as lamellae, are typically less than 100 nm thick.

In a scanning transmission electron microscope (STEM), a primary electron beam is focused to a fine spot, and the spot is scanned across the sample surface. Electrons that are transmitted through the work piece are collected by an electron detector on the far side of the sample, and the intensity of each point on the image corresponds to the number of electrons collected as the primary beam impacts a corresponding point on the surface.

Because a sample must be very thin for viewing with transmission electron microscopy (whether TEM or STEM), preparation of the sample can be delicate, time-consuming work. The term "TEM" as used herein refers to a TEM or an STEM and references to preparing a sample for a TEM are to be understood to also include preparing a sample for viewing on an STEM. The term "S/TEM" as used herein also refers to both TEM and STEM.

Several techniques are known for preparing TEM specimens. These techniques may involve cleaving, chemical polishing, mechanical polishing, or broad beam low energy ion milling, or combining one or more of the above. The disadvantage to these techniques is that they are not site-specific and often require that the starting material be sectioned into smaller and smaller pieces, thereby destroying much of the original sample.

Other techniques generally referred to as "lift-out" techniques use focused ion beams to cut the sample from a substrate or bulk sample without destroying or damaging surrounding parts of the substrate. Such techniques are useful in analyzing the results of processes used in the fabrication of integrated circuits, as well as materials general to the physical or biological sciences. These techniques can be used to analyze samples in any orientation (e.g., either in cross-section or in plan view). Some techniques extract a sample sufficiently thin for use directly in a TEM; other techniques extract a "chunk" or large sample that requires additional thinning before observation. In addition, these "lift-out" specimens may also be directly analyzed by other analytical tools, other than TEM. Techniques where the sample is extracted from the substrate within the FIB system vacuum chamber are commonly referred to as "in-situ" techniques; sample removal outside the vacuum chamber (as when the entire wafer is transferred to another tool for sample removal) are call "ex situ" techniques.

Samples which are sufficiently thinned prior to extraction are often transferred to and mounted on a metallic grid covered with a thin electron transparent film for viewing. FIG. 13A shows prior art TEM grid 10 for mounting a sample. A typical TEM grid 10 is made of copper, nickel, or gold.

Although dimensions can vary, a typical grid might have, for example, a diameter of 3.05 mm and have a middle portion 12 consisting of cells 14 of size 90 µm by 90 µm and bars 13 with a width of 35 µm. The electrons in an impinging electron beam will be able to pass through the cells 14, but will be blocked by the bars 13. The middle portion 12 is surrounded by an edge portion 16. The width of the edge portion is 0.225 mm. The edge portion 16 has no cells, with the exception of the orientation mark 18. The thickness 15 of the thin electron transparent support film is uniform across the entire sample carrier, with a value of approximately 20 nm. TEM specimens to be analyzed are placed or mounted within cells 14.

In one commonly used ex-situ sample preparation technique, a protective layer 22 of a material such as tungsten is first deposited over the area of interest on a sample surface 21 as shown in FIG. 14 using electron beam or ion beam deposition. Next, as shown in FIGS. 15-16, a focused ion beam using a high beam current with a correspondingly large beam size is used to mill large amounts of material away from the front and back portion of the region of interest. The remaining material between the two milled rectangles 24 and 25 forming a thin vertical sample section 20 that includes an area of interest. The trench 25 milled on the back side of the region of interest is smaller than the front trench 24 The smaller back trench is primarily to save time, but the smaller trench also prevents the finished sample from falling over flat into larger milled trenches which may make it difficult to remove the specimen during the micromanipulation operation.

As shown in FIG. 17, once the specimen reaches the desired thickness, the stage is tilted and a U-shaped cut 26 is made at an angle partially along the perimeter of the sample section 20, leaving the sample hanging by tabs 28 at either side at the top of the sample. The small tabs 28 allow the least amount of material to be milled free after the sample is completely FIB polished, reducing the possibility of redeposition artifacts accumulating on the thin specimen. The sample section is then further thinned using progressively finer beam sizes. Finally, the tabs 28 are cut to completely free the thinned lamella 27. Once the final tabs of material are cut free lamella 27 may be observed to move or fall over slightly in the trench. A completed and separated lamella 27 is shown in FIG. 18.

The wafer containing the completed lamella 27 is then removed from the FIB and placed under an optical microscope equipped with a micromanipulator. A probe attached to the micromanipulator is positioned over the lamella and carefully lowered to contact it. Electrostatic forces and vacuum forces will attract lamella 27 to the probe tip 29 as shown in FIG. 19. The tip 29 with attached lamella is then typically moved to a TEM grid 10 as shown in FIG. 20 and lowered until lamella is placed on the grid in one of the cells 14 between bars 13.

Samples which require additional thinning before observation are typically mounted directly to a TEM sample holder. FIG. 13B shows a typical TEM sample holder 31, which comprises a partly circular 3 mm ring. In some applications, a sample 30 is attached to a finger 32 of the TEM sample holder by ion beam deposition or an adhesive. The sample extends from the finger 32 so that in a TEM (not shown) an electron beam will have a free path through the sample 30 to a detector under the sample. The TEM sample is typically mounted horizontally onto a sample holder in the TEM with the plane of the TEM grid perpendicular to the electron beam, and the sample is observed. A common in-situ extraction technique is described in U.S. Pat. No. 6,570,170, to Moore, which describes extracting out a sample by making a "U"-shaped cut and then cutting the sample at an angle from the missing side of the "U" to undercut and free the sample. After the sample is freed, a probe is attached to the sample by FIB-induced chemical vapor deposition and it is lifted out. In other applications, the probe is attached before the sample is freed. This process typically results in a chunk-type sample, which is generally wedge shaped and approximately 10 µm×5 µm×1 µm in size.

Unfortunately, preparation of TEM samples using such prior art methods of sample extraction suffer from a number of shortcomings. Such methods are typically very time-consuming, about 90 minutes/sample, and labor intensive. CD metrology often requires multiple samples from different locations on a wafer to sufficiently characterize and qualify a specific process. In some circumstances, for example, it will be desirable to analyze from 15 to 50 TEM samples from a given wafer. When so many samples must be extracted and measured, using known methods the total time to process the samples from one wafer can be days or even weeks. Even though the information that can be discovered by TEM analysis can be very valuable, the entire process of creating and measuring TEM samples has historically been so labor intensive and time consuming that it has not been practical to use this type of analysis for manufacturing process control.

Specifically, the ex-situ method discussed above can be time consuming and difficult to locate a lamella site and the extraction probe must be very carefully moved into position to avoid damaging the sample or the probe tip. Once a lamella has been completely freed, it can move in unpredictable ways; it can fall over in the trench or in some cases it can actually be pushed up and out of the trench by electrostatic forces. This movement can make it difficult to locate and/or pick up the lamella with the extraction probe. The electrostatic attraction between the probe and the sample is also somewhat unpredictable. In some cases, the lamella may not stay on the probe tip. Instead, it can jump to a different part of the probe. In other cases, the lamella may fall off while the sample is being moved. If the lamella is successfully transferred to the TEM grid, it can be difficult to get the lamella to adhere to the grid support film rather than the probe tip. The lamella will often cling to the probe tip and must be essentially wiped off onto the film. As a result, it can be very difficult to control the precise placement or orientation of the lamella when it is transferred to the TEM grid. The in-situ method described above provides more control but is considerably more time-consuming. A significant amount of time is taken up by the steps of attaching the microprobe to the sample, attaching the sample to the sample holder, and cutting the microprobe free. The sample is also moved to and attached to the TEM grid inside the FIB instrument, which requires more valuable FIB time.

Speeding up the process of sample extraction and transfer would provide significant advantages in both time and potential revenue by allowing a semiconductor wafer to be more rapidly returned to the production line. Full or partial automation of the process of sample removal and transport would not only speed up the process, but it would also reduce the level of expertise required of operators and technicians thus lowering personnel costs.

Because of the precision required to produce thin lamella, the process has not adapted itself to automation. The thinner the lamella, the more difficult it is to automate the extraction process. Lamella under 100 nm in thickness, particularly lamella under 70 nm in thickness, are difficult to produce either manually or in an automated fashion. Slight changes in the positioning of the ion beam can ruin the lamella by producing the lamella at a position that excludes the feature of interest or by altering the thickness. The thin lamella can shift position slightly, which changes the position of the beam relative to the lamella. The thin lamella can also warp during formation, due to mechanical or thermal stress. These factors combine to make the formation of lamella an exceedingly difficult process to automate.

What is needed is an improved method for TEM sample preparation that is robust, repeatable, and can be automated.

SUMMARY OF THE INVENTION

It is an object of the invention, therefore, to provide a robust process that can repeatedly produce thin lamella for viewing on a transmission electron microscope.

In accordance with a preferred embodiment, several techniques are used that together provide a robust process suitable for automation while providing lamella that are accurately placed relative to the feature of interest and that have faces that are parallel to each other and that are preferably orthogonal to surface of the work piece. Not all aspects are required for all embodiments.

In some preferred embodiments, a protective layer having a sputter rate that matches the sputter rate of the substrate is used over the region of interest. Such a protective layer assists in the creation of an orthogonal edge, particularly when using a lower ion energy, e.g., 5 keV, Gallium ion milling. Using this protection prevents lamella from developing a "golf tee" shape directly below the protective layer. When extracting a lamella from a silicon substrate, a carbon protective layer can be used because the carbon milling rate matches the silicon milling rate better than the milling rate of a tungsten protective layer matches the silicon milling rate, particularly at low ion energy milling, such as at 5 KeV. At higher ion energies, the milling rate for silicon and tungsten, while still different, are closer to each other.

Another aspect that contributes to a repeatable process suitable for automation is using a "shelf mill" in which the beam is moved progressively toward the observation face, and as the beam approaches the face, the milling depth is reduced to produce a bottom that slopes away from the feature of interest. This keeps the lower part of lamella thick and structurally sound to facilitate automation by keeping the lamella from moving during thinning.

In another aspect, a fiducial is used to position the beam for the final high ion energy, e.g., 30 keV, mill. In previous methods, the edge of the lamella was used to place the final mill, which was thought to be more accurate because it is referenced directly to the object being cut, and not to a different object. Applicants have found that because the fiducial is more stable and more easily identifiable, using the fiducial instead of the lamella edge improves accuracy, which is useful for automated cut placement. The fiducial provides two edges to average for improved positioning, as opposed to the traditional method of registration based on a single edge of the lamella.

In another aspect, the tabs are completed after high ion energy, e.g., 30 keV, final thinning. This keeps the lamella rigidly coupled to the substrate and therefore keeps it stable relative to the fiducial on the substrate. Any shift in lamella position can lead to thickness or cut placement instability.

In another aspect, the lamella is cut around the edges to product a tab only after all the thinning milling is completed, but before the low voltage polish milling is performed. This provides increased mechanical support during thinning, which makes the lamella more stable and allows more accurate beam placement for thinning.

In another aspect, a defocused low ion energy, e.g., 5 keV, polish and pattern refresh delay (to decrease power delivered to sample), is used for the final cut; this reduces deformation of the lamella.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

The accompanying drawings are not intended to be drawn to scale. In the drawings, each identical or nearly identical component that is illustrated in various figures is represented by a like numeral. For purposes of clarity, not every component may be labeled in every drawing.

DETAILED DESCRIPTION OF PREFERRED EMBODIMENTS

Preferred embodiments of the present invention are directed toward a method for improved control of lamella placement and sidewall orthogonality. This allows fully automated creation of lamella having a thickness of less than 100 nm, less than 70 nm lamella, or less than 50 nm lamella.

Embodiment of the invention as described below produce a lamella in which the thickness of the viewing area of the finished lamella preferably varies by less than 25%, more preferably by less than 10%, and even more preferably by less than 3% over the viewing area. The faces of the finished lamella are preferably orthogonal to the substrate surface within 5 degrees, more preferably within 1 degree and even more preferably within 0.5 degrees.

The viewing area of the finished lamella is typically between 0.2 μm and 5 μm wide and up to 2 μm deep.

Figure 1:
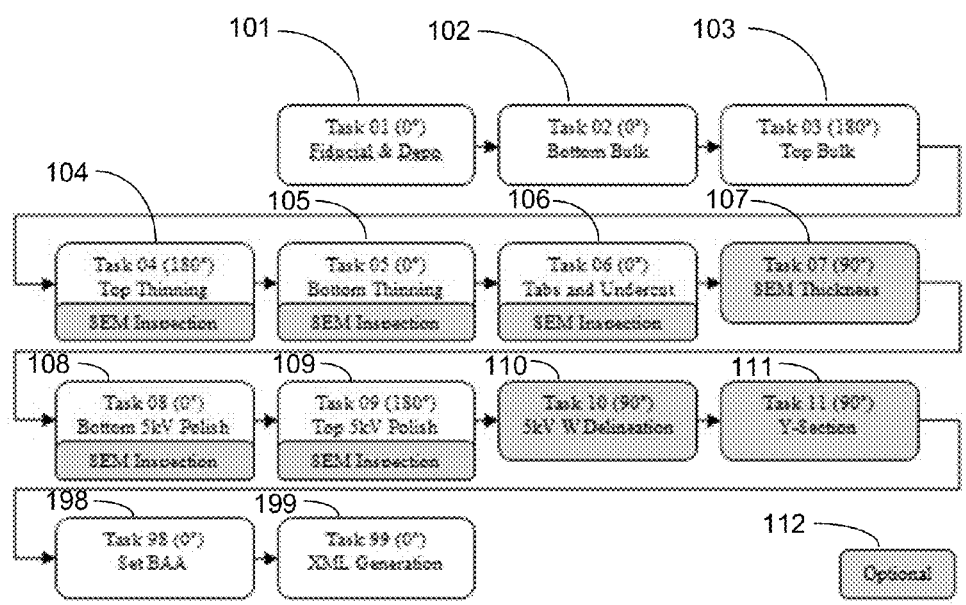
FIG. 1 shows an overview of the 50 nm process according to an embodiment of the present invention.

FIG. 1 shows an overview of a process according to an embodiment of the present invention. The individual steps are described in more detail in subsequent paragraphs. In Step 101 (Task 01), a feature of interest in located and the fiducials are milled such that the desired lamella center is exactly between the fiducials. In Steps 102 and 103 (Task 02 and Task 03, respectively), bottom and top bulk mills are performed symmetrically using the same milling offsets for each mill such that the final result is a uniform wedge-shaped lamella that is centered between the fiducials. In Steps 104 and 105 (Task 04 and Task 05, respectively), top and bottom thinning mills are performed symmetrically by keeping the offset of each mill equal, such that a ledge or "shelf" structure is created on either side of the lamella below the thinned window. In Step 106, (Task 6), the first of two tab mills removes the top third of the total lamella height. Then the second of the two tab mills removes the bottom third of the total lamella height. An undercut mill also detaches the bottom of the lamella from the substrate. In optional Step 107 (optional Task 07), the lamella thickness is measured in a top-down image as a process monitoring step. The top-down measurements can be calibrated by reference to Y-Section measurements, that is, measurements of a cross-sectioned lamella, although cross-sectioning the lamella renders it unusable for characterizing the semiconductor manufacturing process. In Steps 108 and 109 (Task 08 and Task 09, respectively), low kV polish symmetrically removes the amorphous damage layer created by the beam of the undercut mill. By low kV is meant less than about 10,000 kV, more preferably less than 7,500 kV, and most preferably about 5,000 kV or less. In optional Step 110 (optional Task 10), if the lamella is to be cross-sections to characterize the lamella creation process, a low kV tungsten delineation step minimizes the impact of the Y-Section on the geometry of the lamella and helps demark the edges of the lamella for the Y-Section. In Step 111 (optional Task 11), the lamella is cut in the center of the thinned window providing a direct measurement of the lamella thickness but destroying the lamella in the process. In Tasks 04, 05, 06, 08, and 09, an optional step of inspecting the sample with the SEM can be performed at the beginning and/or end of each step for monitoring the lamella creation process.

Figure 2A:
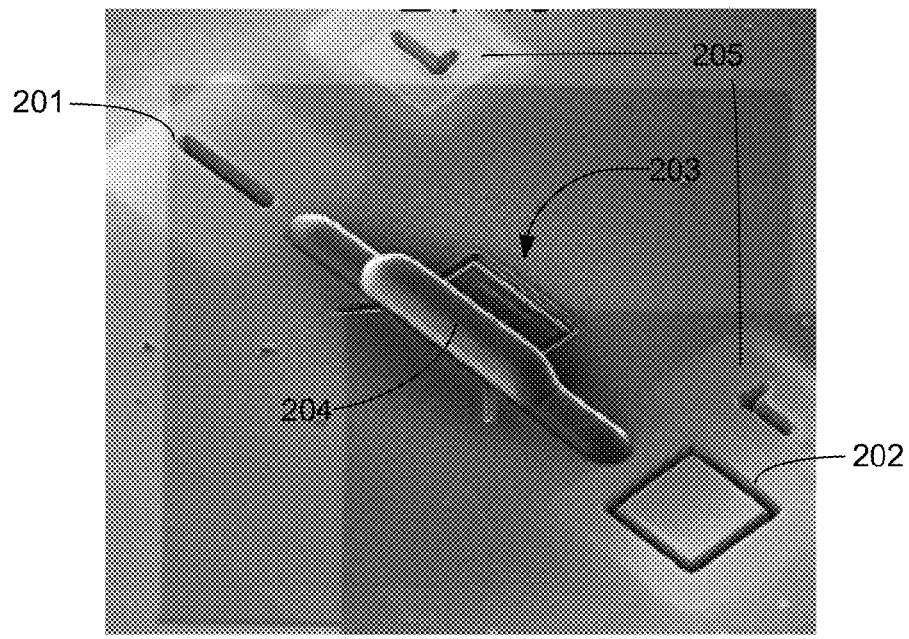
FIGS. 2A and 2B are images of the lamella after Task 01.
Figure 2B:
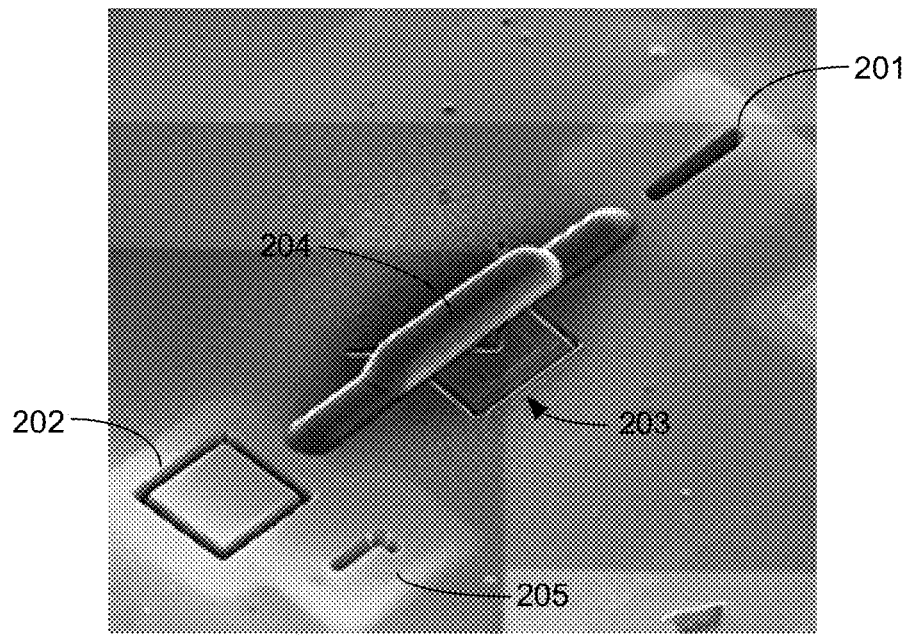

FIGS. 2A and 2B are images of the lamella 204 after step 101. In Step 101, a feature of interest 203 is located and the fiducials 201, 202 are milled with the ion beam such that the desired lamella center 204 is preferably exactly between the fiducials 201, 202. The line fiducial 201 will be used to position the bulk patterning steps and the square fiducial 202 will be used for the placement of the final thinning patterns.

The placement of these features will define the lamella placement, so great care should be exercised to ensure the accuracy and repeatability of these patterns in relation to the feature of interest. The feature of interest is located using features that are visible on the surface of the work piece and computer aided design drawings of the circuit that located the feature of interest, which may not be visible, relative to the visible surface features.

Two Drift Corrected Milling (DCM) marks 205 are created at the beginning of this task. These are used by the DCM algorithm to compensate for any drift that may happen during milling or even between the registration image and the pattern initiation. Drift control algorithms are described, foe example, in U.S. Pat. Pub. No. 20090218488 of Andrew Wells for "Beam Positioning For Beam Processing," which is assigned to the assignee of the present invention.

The DCM marks 205 are placed prior to the fiducials 201, 202 and are utilized while creating the fiducials 201, 202 to ensure the best accuracy possible. The fiducials 201, 202 are preferably milled, one on either side of the desired lamella 204. The fiducials 201, 202 can be in line with the lamella 204 or offset by a known amount.

It is known to apply a protective layer to the region being processed to protect the region of interest. When a protective layer that is harder than the work piece is used, the protective layer causes the top of very thin lamella to have a "golf tee" profile when observed in a Y-Section. Tungsten is a harder, denser material than silicon and has a significantly lower etch rate, which causes the tungsten cap to be wider than the lamella. A carbon protective layer, used instead of a tungsten layer, has a etch rate more closely matches that of silicon. A "matching" sputter rate as used herein means that the ratio of sputter rates of the two materials is preferably less than 1.5:1 and more preferably less than 1.2:1 under the conditions used to mill the cavities described above. When forming a lamella in a semiconductor work piece, it is preferred to use a protecting layer having a matching etch rate, such as a carbon deposition as the protective layer on silicon. A matching sputter rate also reduces curtaining, an artifact on the lamella that can interfere with imaging.

While the protective layer over the region of interest preferably has a sputter rate matching that of the work piece, the protective layer away from the region of interest, where the fiducials are milled, can be of made of a material, such as tungsten, having a lower sputtering rate to preserve the fiducial during the times that the beam is directed to the fiducial as a position reference.

Figure 3A:
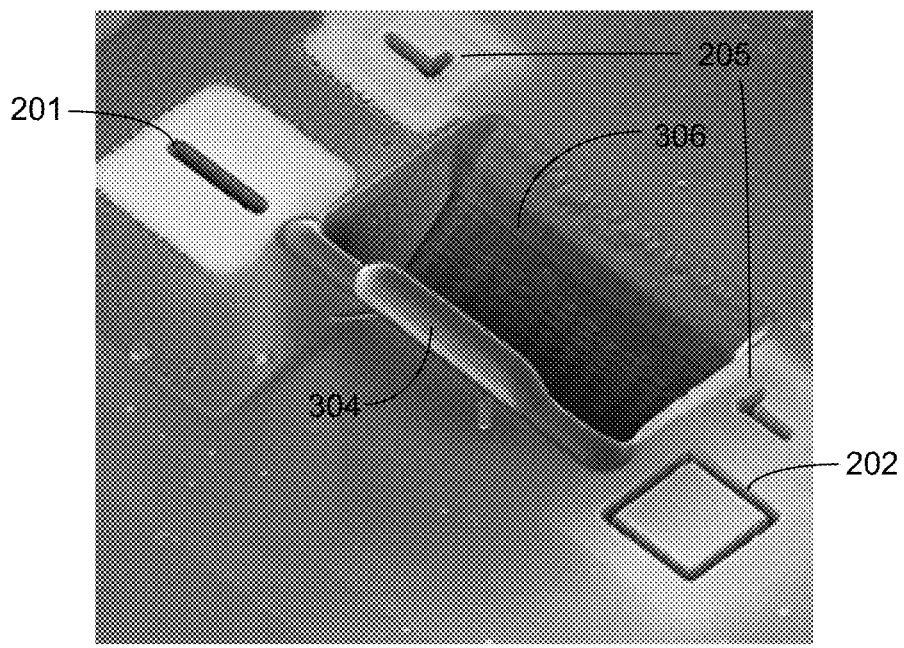
FIGS. 3A and 3B are images of the lamella after Task 02.
Figure 3B:
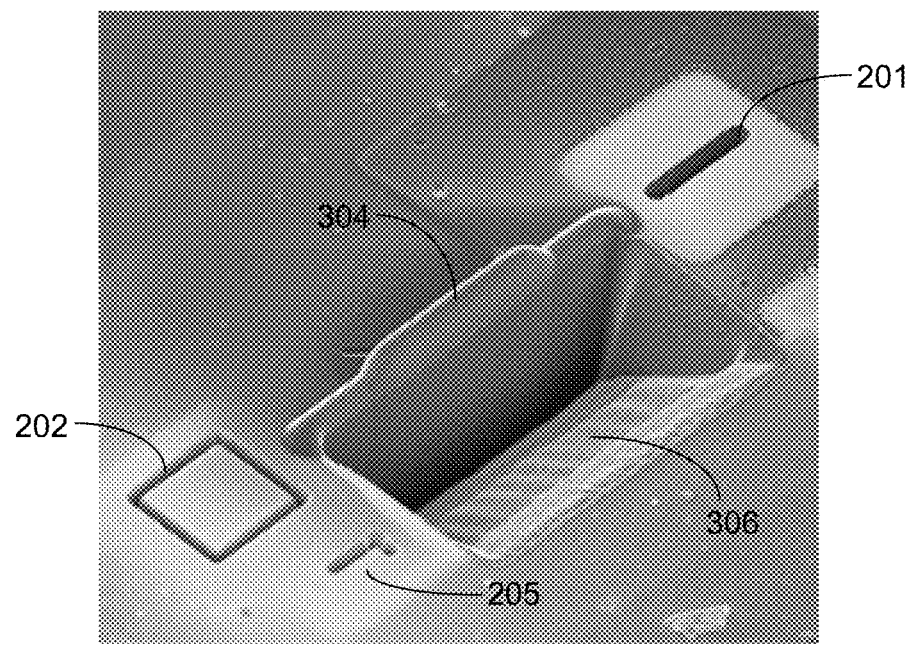
Figure 4A:
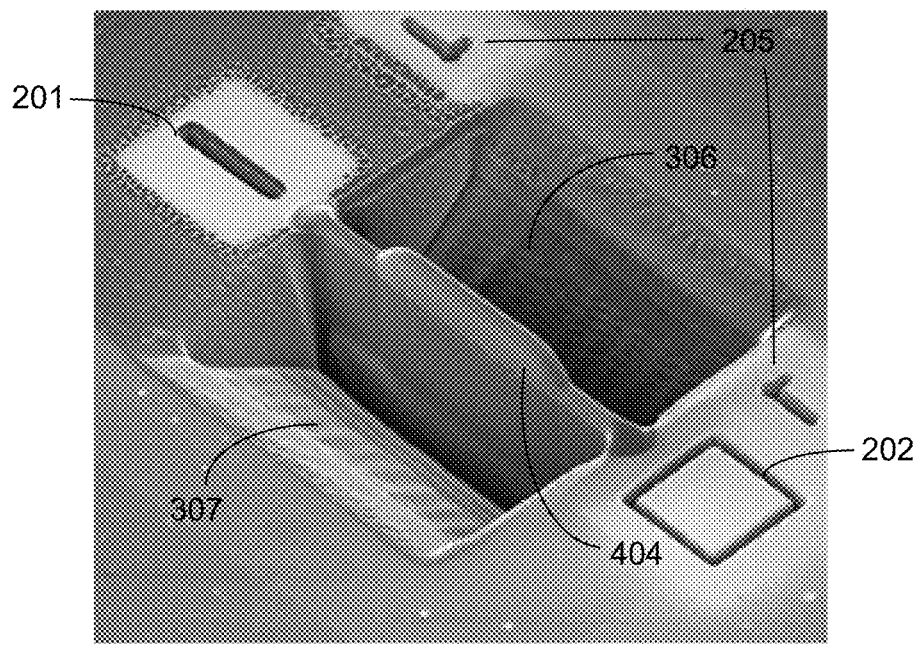
FIGS. 4A and 4B are images of the lamella after Task 03.
Figure 4B:
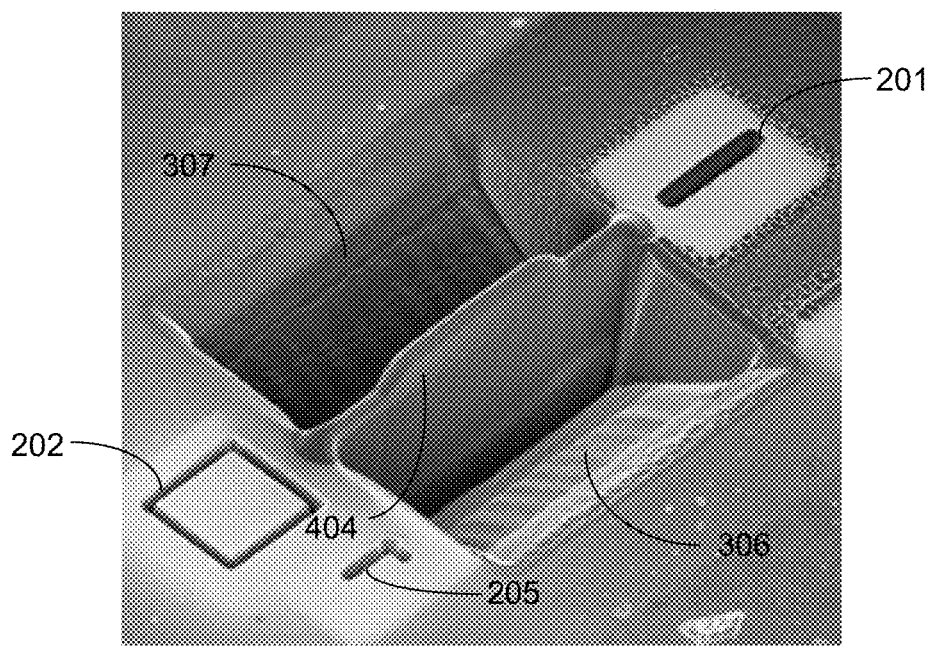

FIGS. 3A and 3B are images of the lamella 304 after milling the bottom bulk in step 102. FIGS. 4A and 4B are images of the lamella 404 after top bulk milling in step 103. In Steps 102 and 103, a bottom bulk mill 306 and a top bulk mill 307 are performed symmetrically, that is, they use the same milling strategy on either side of the lamella 304, 404 and are designed to use the same milling offsets such that the final result is a uniform wedge-shaped lamella 404 that is centered between the fiducials 201, 202.

The bulk mill is typically performed at a relatively high beam current, such as between 3 nA and 30 nA, more preferably between 5 nA and 20 nA, even more preferably between about 8 nA and 15 nA, and in some embodiments, at a beam current of about 12.2 nA. Such high beam currents would destroy the DCM marks 205 is the beams were directed toward the DCM for the 30 seconds required for the mills. To minimize the effect of any residual stage motion, the bulk mill is split in three passes with a re-registration between each pass. The three bulk passes consists of: a regular cross section which removes the majority of the material on either side of the lamella, a hole cleaning small rectangle box mill (about 3 microns or less) which removes some redeposited material from the bottom of the holes and generally makes the lamella pockets better prepared for the ex-situ plucker needle, and a cleaning cross section which defines the edge of the bulk lamella faces with great accuracy.

Figure 5A:
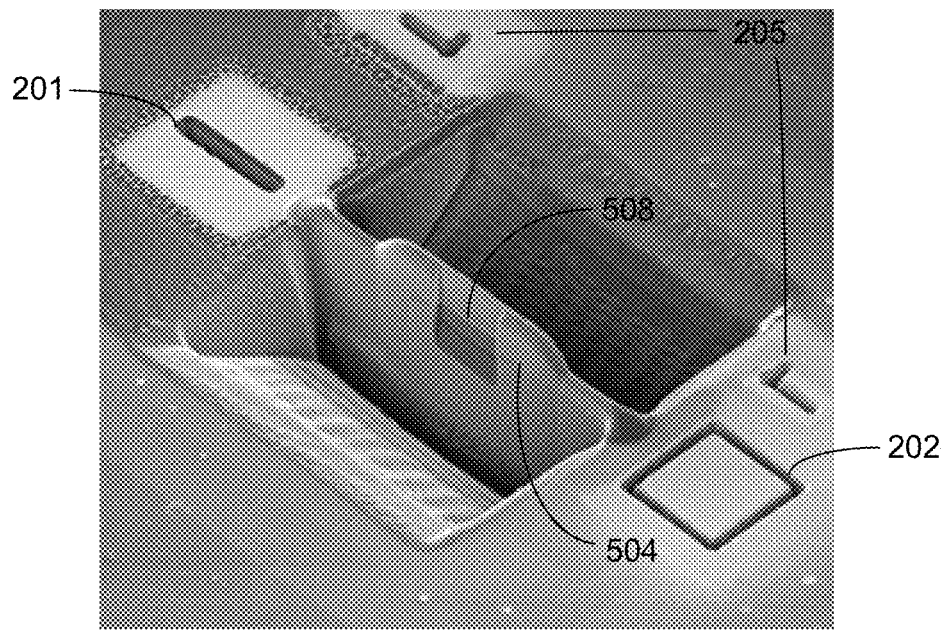
FIGS. 5A and 5B are images of the lamella after Task 04.
Figure 5B:
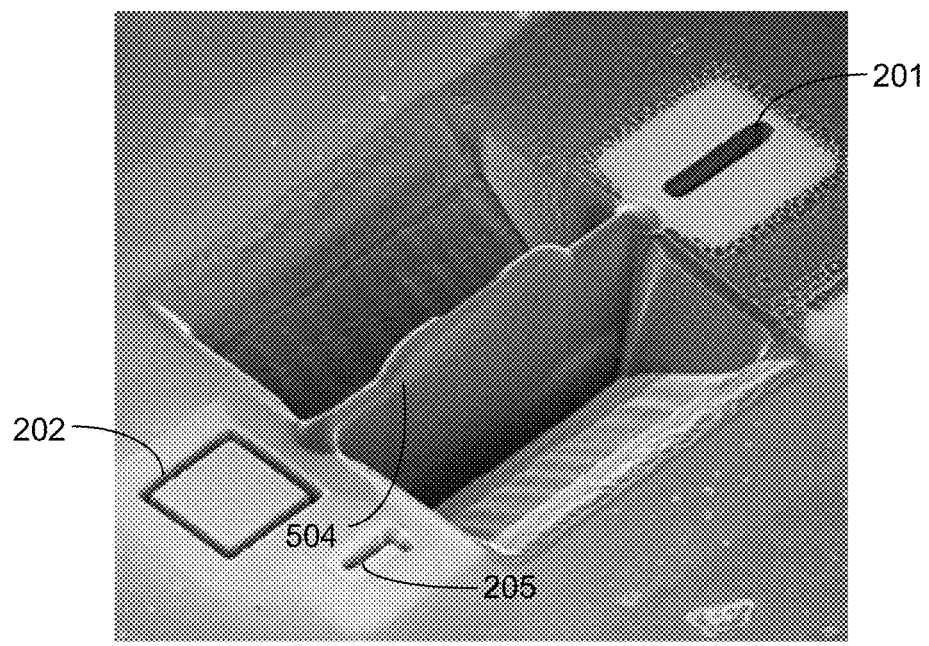
Figure 6A:
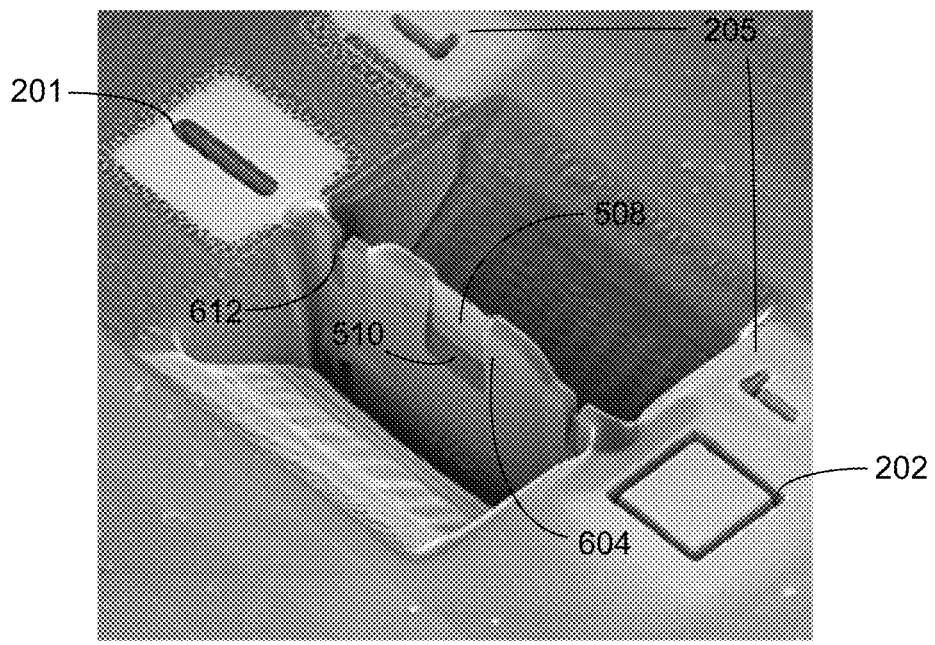
FIGS. 6A and 6B are images of the lamella after Task 05.
Figure 6B:
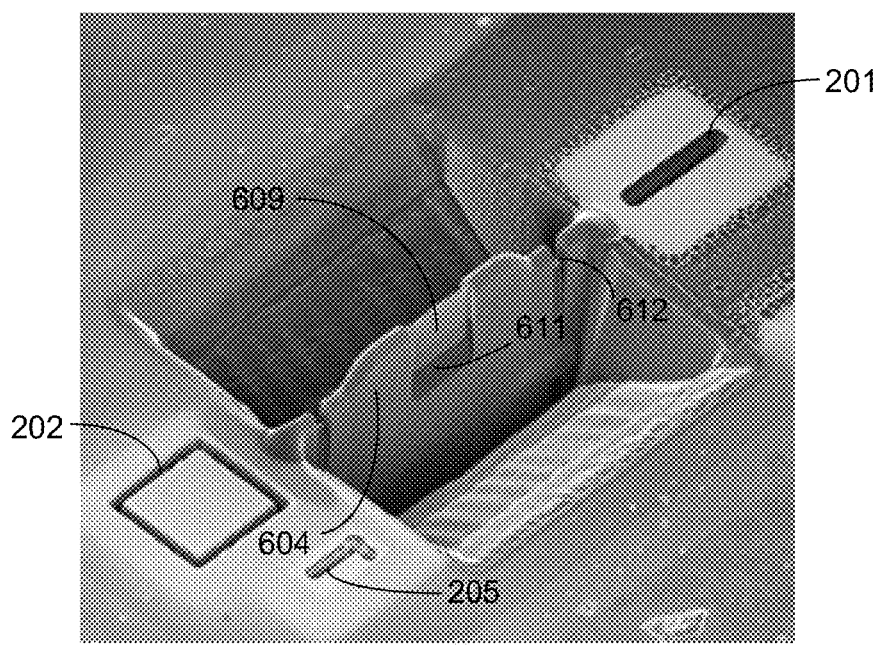

FIGS. 5A and 5B are images of the lamella 504 after top thinning in Step 104. FIGS. 6A and 6B are images of the lamella 604 after bottom thinning in Step 105. In Steps 104 and 105, a top thinning mill 508 and a bottom thinning mill 609 are also symmetrical and the mill offsets are kept equal.

The thinning mills 508, 609 leave a ledge 510, 611 or "shelf" on either side of the lamella 504, 604 below the thinned window 508, 609. This ledge 510, 611 adds to the structural integrity of the lamella 504, 604, which helps to keep it from fracturing during lift-out. The ledge structure 510, 611 is created by using a cleaning cross-section whose dose is only enough to remove re-deposited sputtered material and about 1 um of the underlying material as described below. After the cleaning cross-section, there is a longer line mill at the lamella face that ensures that the thinned window 508, 609 is vertical. The line mill is typically performed using a high beam energy, a beam current of less than about 100 pA, and a beam tilt of about 1 degree.

The ledge structure 510, 611 can be created by starting a top-down line raster pattern parallel to the lamella face just off the bulk lamella. The line pattern is moved towards the cut face in small increments. The dose of the line raster should be such that it only removes the top about 1 micron of the lamella 504, 604. The position of the line raster continues incrementing towards the desired final lamella face. Each subsequent cut removes less material than the previous cut because the angle of incidence of the beam at the bottom of the cut is greater than the glancing angle at which the beam impacts the side wall so the bottom mills slower. The final line raster that defines the lamella face will have a dose about 2-3 times higher than the previous rasters to make the lamella faces orthogonal to the wafer surface.

The cleaning cross section can be thought of as a line mill that slowly advances towards the final cut face position: the beam sweeps back and forth across a line parallel to the desired final cut face and at intervals the line is advanced towards the desired final cut face until it is reached. The intervals are determined by the dose of the mill. The dose is usually measured in nano coulombs per square micrometer and is essentially a way of defining how many ions impact the work piece per unit area. When using cleaning cross-sections, a dose is typically set that ensures that the material all the way from the top of the cut face down to the bottom of the trench is removed before the line scan is incremented. However, in this process a dose is selected such that each line scan only removes a portion of the cut face, and each line is shallower than the previous line. The dose per line is constant, but because of the dynamics of grazing angle sputtering, each line is shallower since the previous line didn't remove all the material along the cut face which leads to a slope away from the desired final cut face at the bottom. This effect compounds since the dose of the next line is not high enough to remove all the material on the cut face and there is a slope at the bottom. Since the sputter rate of materials is generally highest at grazing angles with sharply decreasing sputter rate as the beam approaches a more orthogonal angle of incidence, the amount of material removed from the slope is less that the amount removed from the sidewalls.

The lamella sidewalls are preferably vertically oriented and parallel. At the end of the shallowing cleaning cross section, however, the lamella is thin at the top but gets wider at the bottom. The sidewalls are straightened by performing a final line mill with a dose of 2-3 times the dose as the shallowing cleaning cross section, and the wide section at the bottom of the lamella prevents the entire shelf (the thick region below the thinned window) from being removed. This contributes to the verticality of the lamella face.

Alternatively, but less desirably, one can create a thick bulk lamella (about 1 µm to 1.5 µm thick) by placing a line raster pattern inside the outer edge of the bulk lamella. The dose of the line pattern will increase the mill depth at each increment, but shall not mill all the way through the bulk lamella. The line raster pattern is stopped prior to reaching the final cut face. In this case, the bulk lamella is made a little thicker and instead of starting off the lamella (to take advantage of the grazing angle sputter rate) with a dose tuned for shallowing depth, the 95 pA thin mill started on top of the lamella and was tuned to have a decreasing depth.

The accuracy of the high ion energy thinning steps in Step 104 and Step 105 is important. A high ion energy is preferably between 15 keV and 50 keV, more preferably between 20 keV and 40 keV, even more preferably between 25 keV and 35 keV, and most preferably about 30 keV. The low kV polish steps are tuned to remove the amorphous damage layer on the thinned window 508, 609, that is, the polish steps should remove just sufficient material to get rid of a layer damages by previous ion milling steps. The final lamella thickness is defined by the mill offsets in Task 04 and Task 05.

The first of the tab mills 612 is done at the end of Step 105. A filled low energy rectangle mill completely covers the lamella 604. The dose is tuned to remove the top third of the total lamella height, so the position of this mill in not critical. The bounds of the low energy rectangle mill cover the shelf 611, the thinned window 609, and even stretches a short distance past 609 over the top of the protective layer. The goal of this is to expose the entire area to a shower of low-energy ions to remove the amorphous layer created by the 30 kV beam. The low energy polish mill is intentionally larger than the thinned window to better tolerate the mill placement inaccuracies inherent in the low energy beam, but it is only slightly larger than the thinned window 609 and preferably does not go all the way to the tabs 612.

Figure 7A:
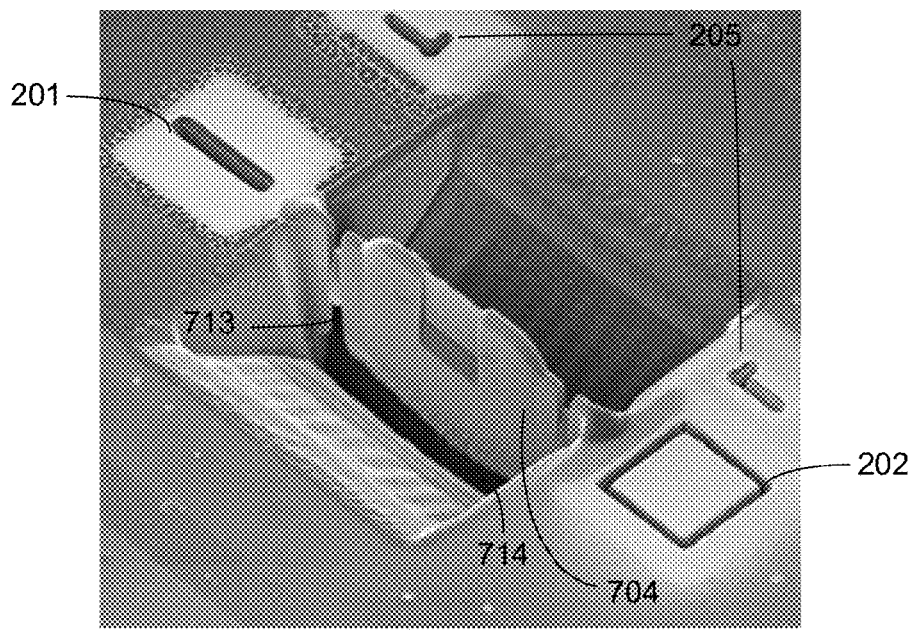
FIGS. 7A and 7B are images of the lamella after Task 06
Figure 7B:
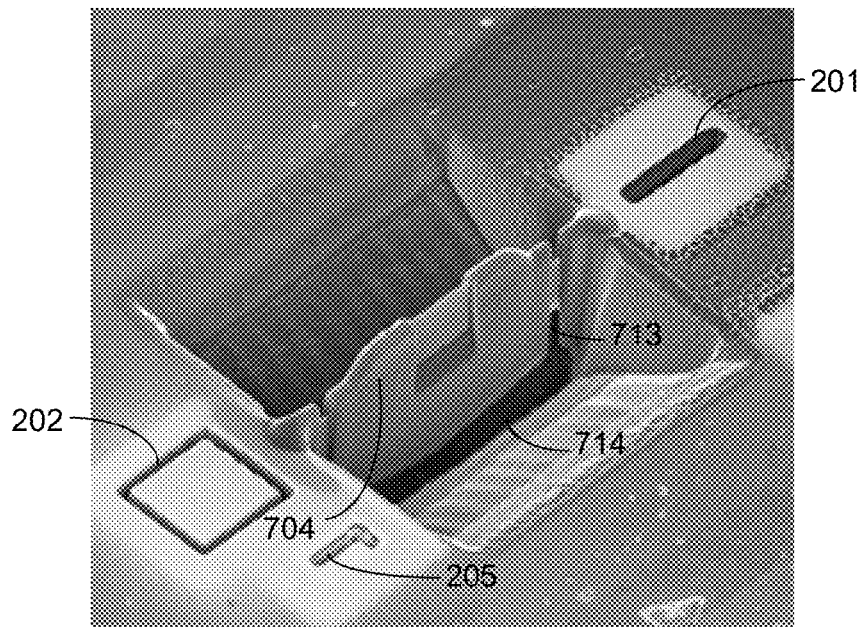

FIGS. 7A and 7B are images of the lamella after Step 106. The second of the tab mills 713 is designed to remove the bottom third of the total lamella height. The placement of this mill 713 is critical: cut too far and the lamella may become detached and cut too little and the tabs may not break.

The undercut mill 714 detaches the bottom of the lamella 704 from the substrate. There is a bridge of material at the bottom of the lamella that is created by the second bulk mill step. It is trimmed from the same side as the first bulk mill.

The tabs 612, 713 and undercut 714 are done after the final 30 kV thinning tasks so that the lamella 704 remains as rigidly affixed to the substrate as possible during the position-critical thinning steps. When the lamella 704 is released at the bottom and the tabs are cut, the lamella 704 may shift with respect to the fiducials 201, 202. Since the mills are all placed relative to the fiducials 201, 202, the amount of lamella shift will translate directly to thickness or placement repeatability. The low kV cleaning process is not as sensitive to this since the low kV beam illuminates the whole thinned window and removes material relatively uniformly. The position of the beam during the low kV cleaning step is not critical. The low kV polishing step is preferably performed after step 106 to remove any material deposited onto the lamella face during prior high voltage milling steps. Low kV cleaning is also needed to reduce thickness while minimizing the amorphous damage due to the previous 30 kV steps. The primary reason the low energy mill is performed last is to limit the amorphous layer. Once the low energy polish is performed, the work piece is preferably not subject to any high energy ions, which would risk increasing the damage layer. Avoiding high voltage ions includes avoiding using the ion beam for images that are required to position the mills that create the tabs.

Figure 8A:
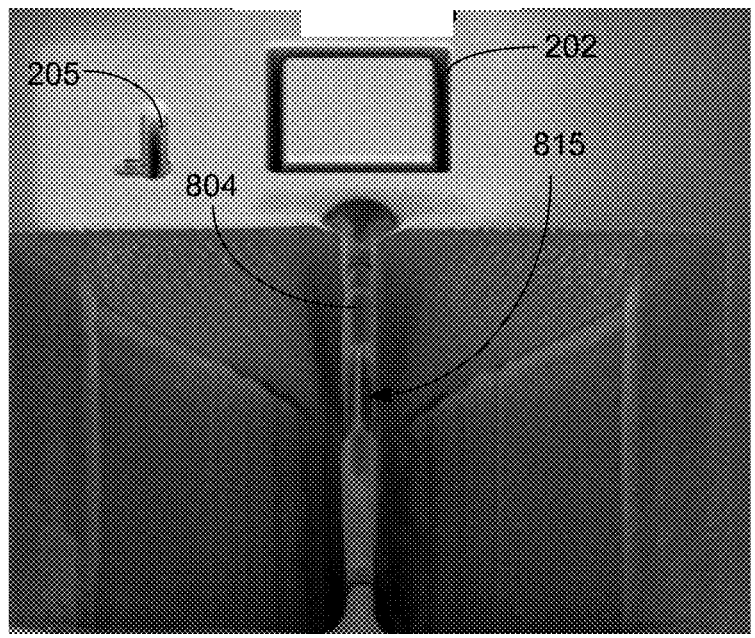
FIG. 8A is an image of the SEM top-down thickness measurement in optional Task 07.
Figure 8B:
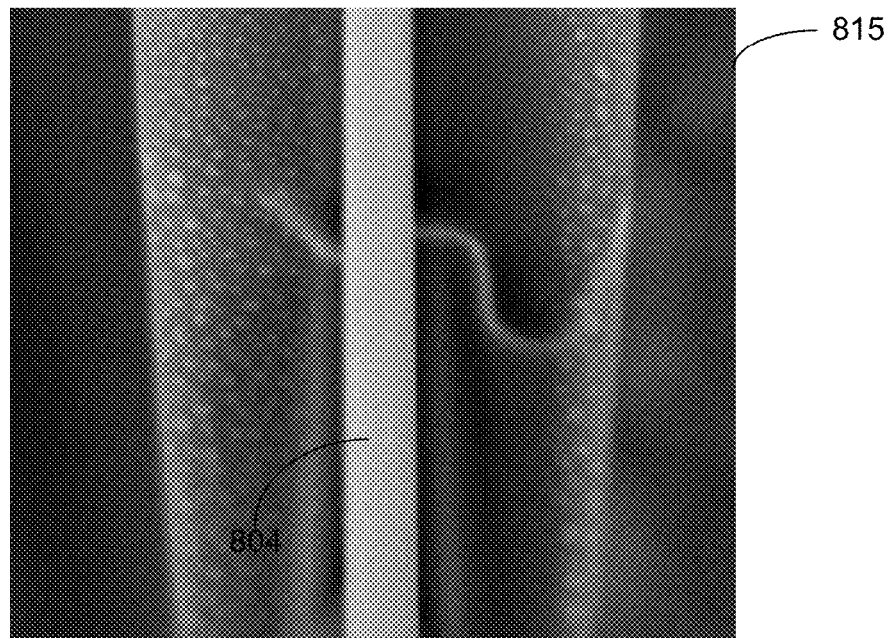
FIG. 8B is a magnified image of the region of the lamella used in the thickness measurement in optional Task 07 according to one embodiment of the present invention.

FIG. 8A is an image of the SEM top-down thickness measurement in optional Step 107. FIG. 8B is a magnified image of the region 815 of the lamella 804 used in the thickness measurement in optional Step 107 according to one embodiment of the present invention.

Optional Step 107 has a top-down lamella thickness measurement that is intended for use as a process monitoring step once the lamella thickness has been calibrated using destructive Y-Section measurements. To make Y-Section measurements, the wafer is rotated 90 degrees such that the tilt axis of the SEM is lined up with the length of the lamella 804. The more accurate measurement of the thickness of the cross section is used to calibrate the top-down SEM thickness measurement. The SEM top-down technique is useful for routine monitoring because the thickness at this stage appears to be a good predictor for the final thinned thickness, and the top-down SEM measurement is non-destructive. The prediction will not be perfect and may vary tool-to-tool but should be sufficient to monitor for process excursions.

For forming lamella of semiconductors using a carbon protective layer, the top-down SEM metric works well after the 30 kV polish but the low kV process induces some deformation in the top of the carbon that renders the measurement inaccurate.

This task is not required to create the lamella 804 and may be skipped to increase lamella throughput. It is preferred, however, to periodically perform a Y-Section and compare the measurement to the top-down SEM measurement to calibrate the top-down SEM, and then periodically to monitor thickness stability.

Figure 9A:
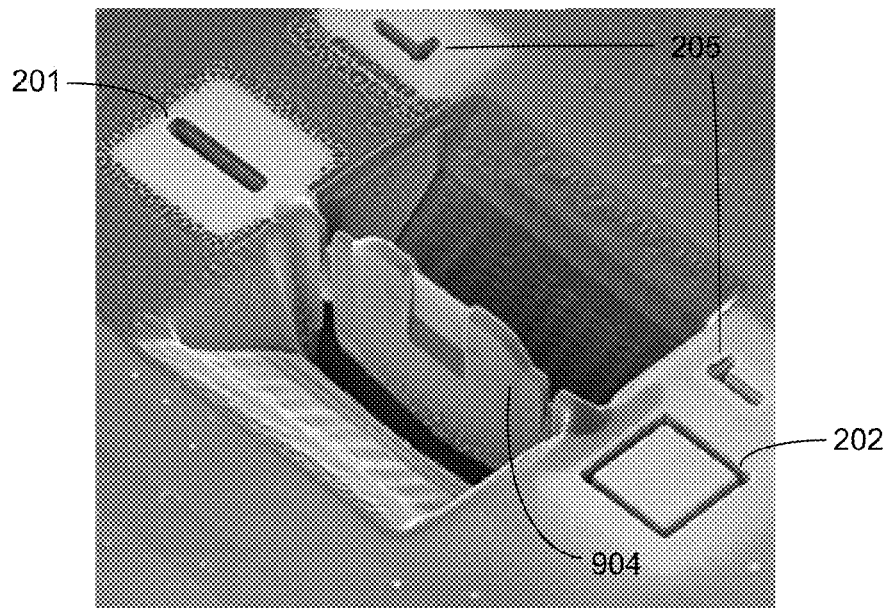
FIGS. 9A and 9B are images of the lamella after Task 08.
Figure 9B:
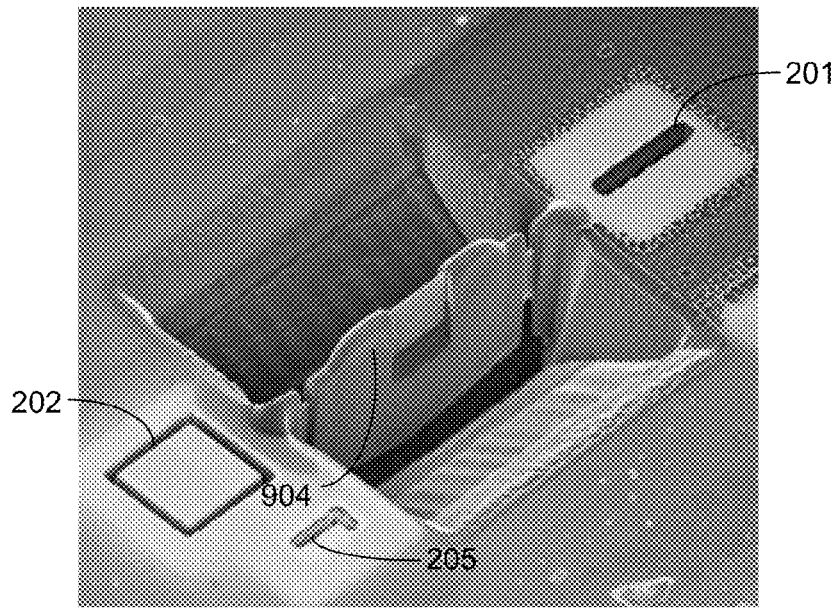
Figure 10A:
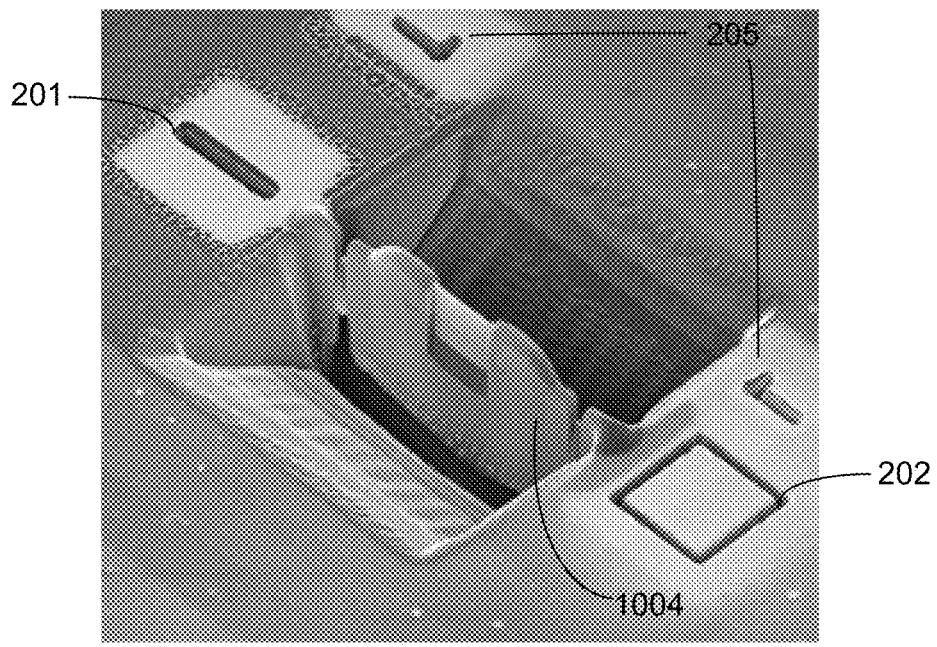
FIGS. 10A and 10B are images of the lamella after Task 09.
Figure 10B:
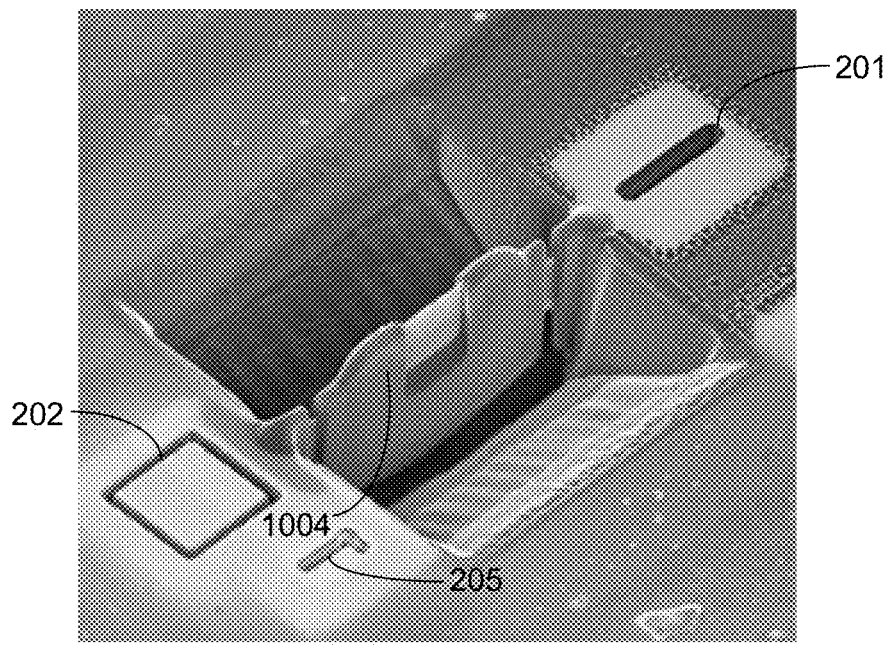

FIGS. 9A and 9B are images of the lamella after Step 108. FIGS. 10A and 10B are images of the lamella after Step 109. The low kV polish steps are symmetric and are designed to remove the amorphous damage layer created by the higher energy, typically 30 keV, beam. The beam illuminates the whole thinned region and the amount of material removed is defined by the dose applied to the area.

When performing the low kV polishing step on a semiconductor having a carbon protective layer, it was preferable to defocus the beam and use a pattern refresh delay. With the beam at best focus and/or without the pattern refresh delay additional deformation of the lamella thinned window was observed. The beam is defocused so that the spot size increases by more than 25%, by more than 50% or more preferably by more than 100%.

A "pattern refresh delay" means that the duty cycle is less than 100%. The delay is provided when the beam is not incident on the material being thinned. The reduced duty cycle allowing for the incident energy to dissipate from the region being thinned.

The duty cycle may be reduced, for example, to less than 80%, less than 50%, less than 25% or less than 15%. Applicants have found that a duty cycle of about 20% produces a lamella with reduced deformation. That is, after the beam is scanned, a delay is imposed before the beam is scanned over the same region again.

In some realizations of the invention, this reduction in effective duty cycle on the thinned window could also be achieved by enlarging the scan region to an appropriately large value.

Figure 11A:
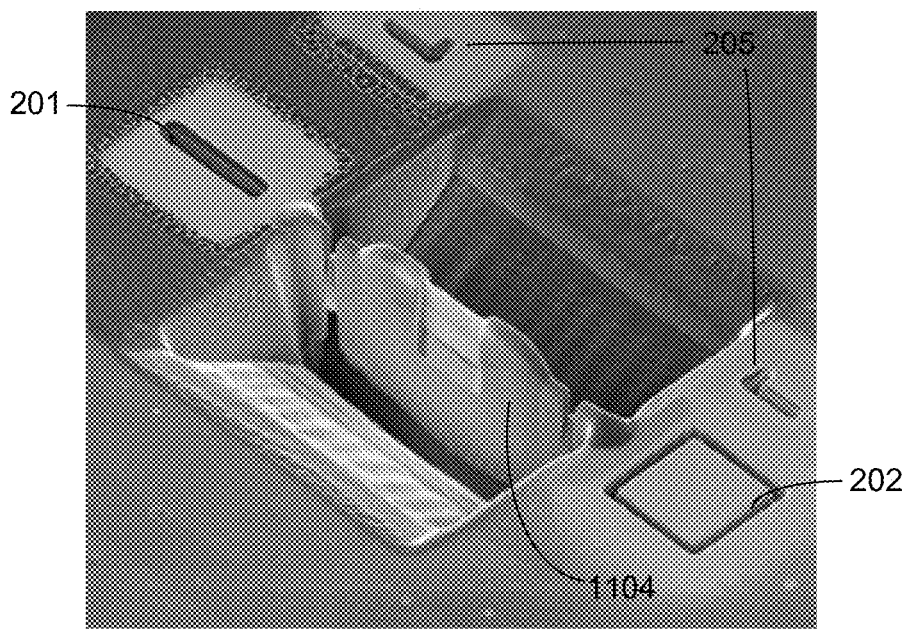
FIGS. 11A and 11B are images of the lamella after Task 10.
Figure 11B:
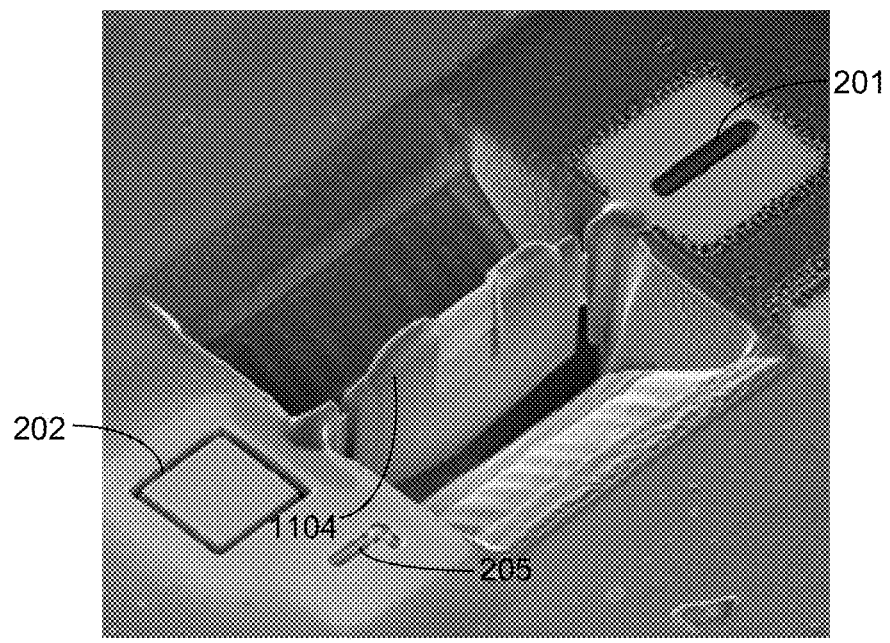

FIGS. 11A and 11B are images of the lamella after optional Step 110. In optional Step 110, a low kV tungsten delineation step was designed to minimize the impact of the 30 kV Y-Section on the geometry of the lamella and to help demark the edges of the lamella for the Y-Section (particularly the semiconductor branch of the process).

This process is intended to be used in conjunction with the Y-Section task. Running this task will render the lamella useless, so it should be disabled except when creating Y-Section measurements.

Figure 12A:
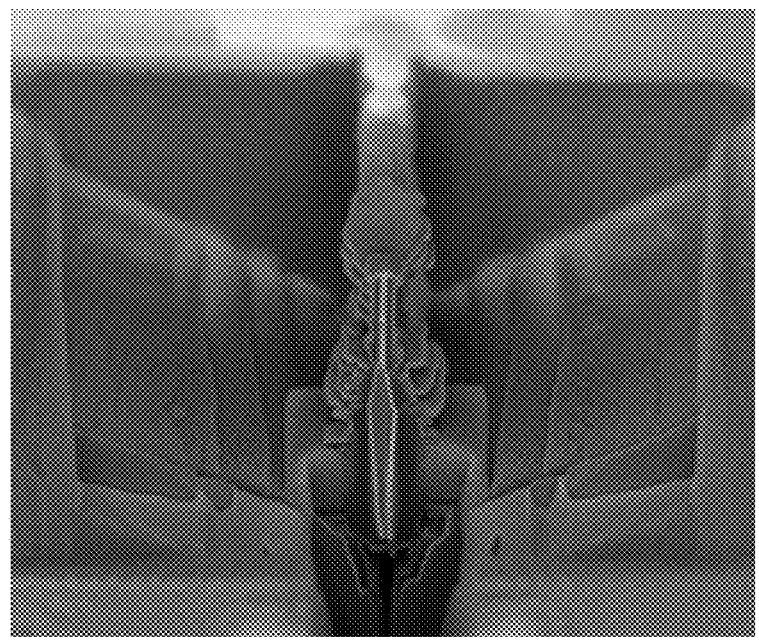
FIG. 12A is an image of the Y-section measurement in Task 11.
Figure 12B:
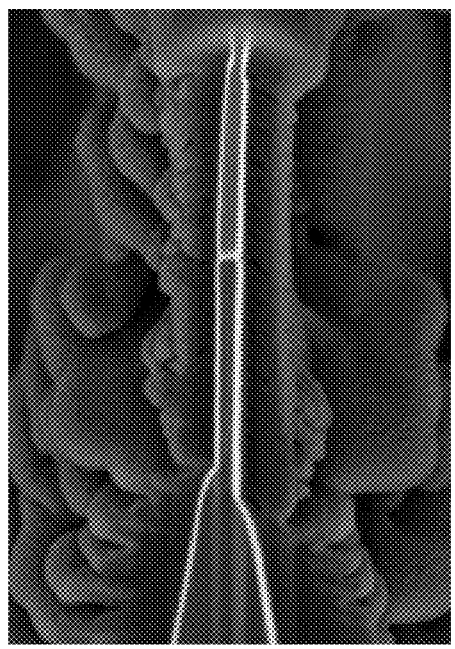
FIG. 12B is a magnified image of cross section of the lamella used in the Y-section measurement in Task 11.
Figure 13A:
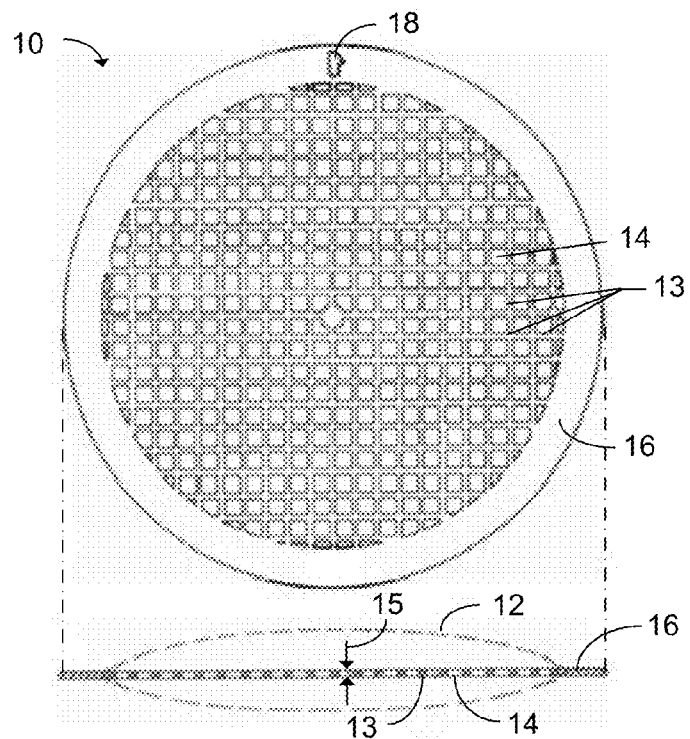
FIGS. 13A and 13B show a typical prior art TEM grid.
Figure 13B:
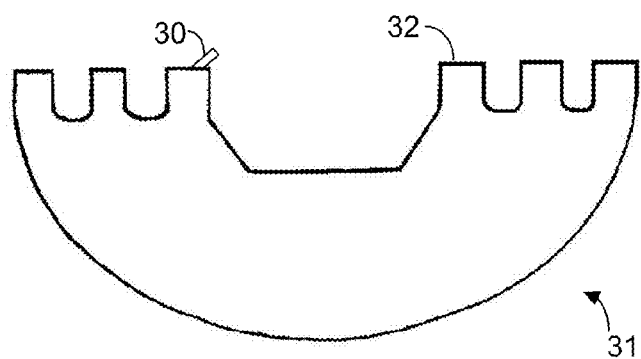
Figure 14:
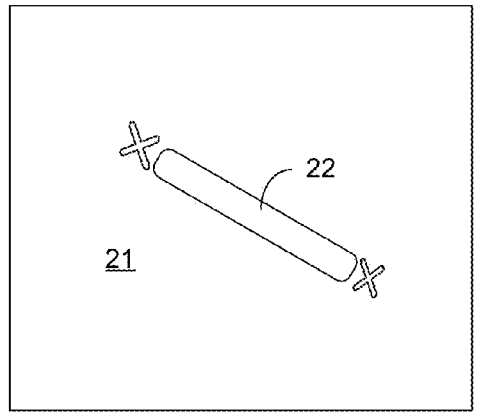
FIGS. 14-17 illustrate the steps in an ex-situ sample preparation technique according to the prior art.
Figure 15:
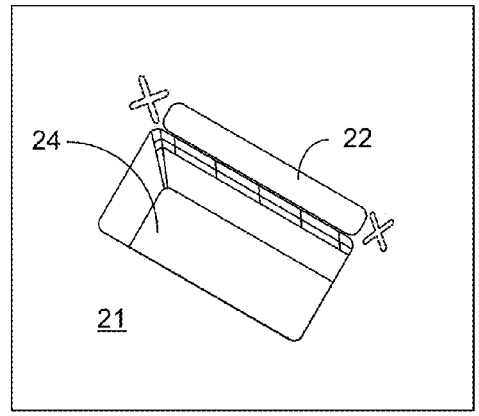
Figure 16:
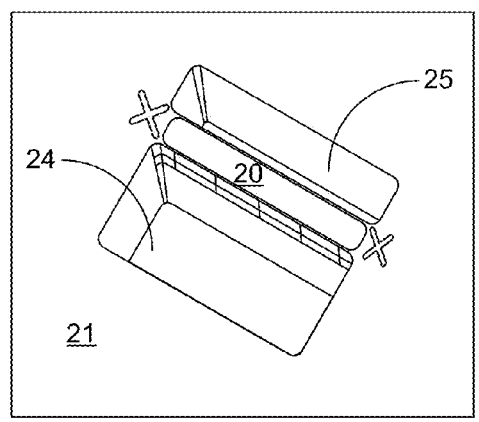
Figure 17:
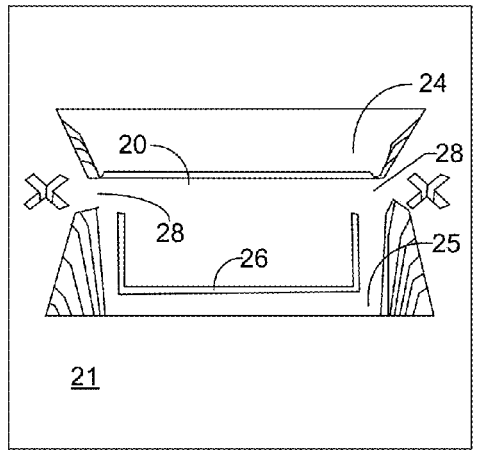
Figure 18:
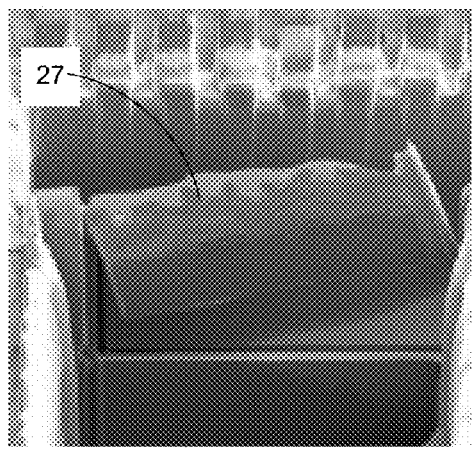
FIG. 18 is a micrograph of a completed and separated lamella according to the prior art.
Figure 19:
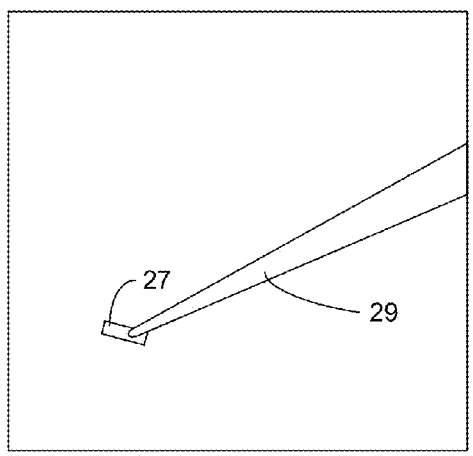
FIGS. 19-20 illustrate the transfer of a lamella using a probe and electrostatic attraction according to the prior art.
Figure 20:
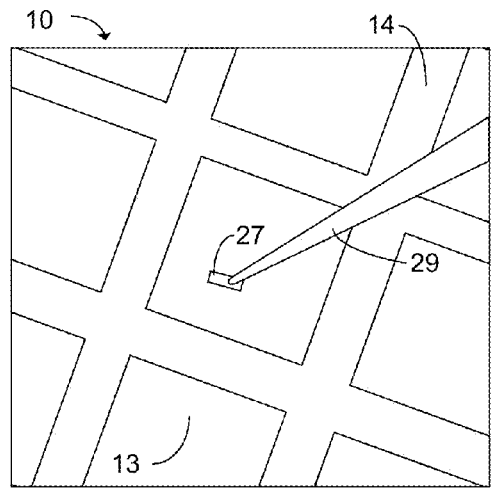

FIG. 12A is an image of the Y-section measurement in optional Step 111. FIG. 12B is a magnified image of cross section of the lamella used in the Y-section measurement in optional Step 111.

Optional Step 111 cuts the lamella in the center of the thinned window. This provides a direct measurement of the lamella thickness but destroys the lamella in the process. This should be used to dial in a process and occasionally to validate the lamella thickness.

The lamella placement accuracy and repeatability is largely dependent on the geometry of the feature of interest. With regard to lamella placement, edge finders are generally more accurate than pattern matching for determining the fine location of features. Pattern matching should be used to coarsely locate features and edge finders should be used for fine location whenever possible. Also with regard to lamella placement, the pixel density of the registration image is critical to the accuracy and repeatability of feature location. Machine vision accuracy is typically quoted in fractions of a pixel, so smaller pixel spacing will typically result in better accuracy. This is limited by the probe size of the beam. The pixel density is a function of the HFW and the image resolution.

SEM deposition of the protective layer can be used to protect sensitive surfaces from FIB damage, but this can lead to lamella placement issues unless a recognizable mark is visible to the FIB after the feature if interest has been covered with SEM deposition.

The fiducial should be located accurately in relation to the feature of interest. Any inaccuracy in feature registration will translate directly into lamella placement error. The fiducial can be placed using existing metrology data, for example, from a tool that locates a defects or from CAD data.

The total dose applied to mill the cavities may need to change to account for the sputter rate(s) of the material(s) in the work piece. The bulk mills should expose a cut face 0.5-1.0 μm deeper than the intended lamella. In some embodiments, a user experiment to determine the mill depth and adjust the ion dose before forming the desired lamellae. The bulk mill doses should be symmetrical unless there is something about the work piece that requires them to be asymmetric (such as a metal pad on one side but not the other), and in this case the doses should be tuned to expose the same depth on both sides.

The thinning mills should cut a vertical cut face about 1 μm deep below the wafer surface.

The primary purpose of the low kV clean mills is to remove the FIB-induced damage layer (also called the amorphous layer) created by the bulk and thin mills. It is therefore important to be familiar with the substrate material and know the approximate difference in the damage layer thickness between 30 kV and 5 kV (for instance, the Si damage layer at 30 kV is about 25 nm and the damage layer at 5 kV is about 6 nm, for a difference of about 19 nm). The goal of the low kV clean mills is to remove slightly greater than the damage layer difference from each side. To set the target thickness for the 30 kV thinning tasks add twice the damage layer difference to the desired lamella thickness (for Si the 30 kV target will be 50 nm+2*19 nm=about 88 nm).

After the lamella is prepared, it is mounted in a TEM sample grid for viewing. The removal of the lamella from the work piece can be performed "ex-situ," that is, outside of the vacuum chamber or the lamella can be removed inside the vacuum chamber and mounted to a grid using ion beam deposition. For ex-situ removal, many lamella can be prepared on a single work piece, which is then removed from the vacuum chamber. The lamella can be removed from the work piece and placed onto TEM sample grids. The process described above can be automated to prepare in the vacuum chamber multiple lamella at various designated locations for ex-situ removal.

Figure 21:
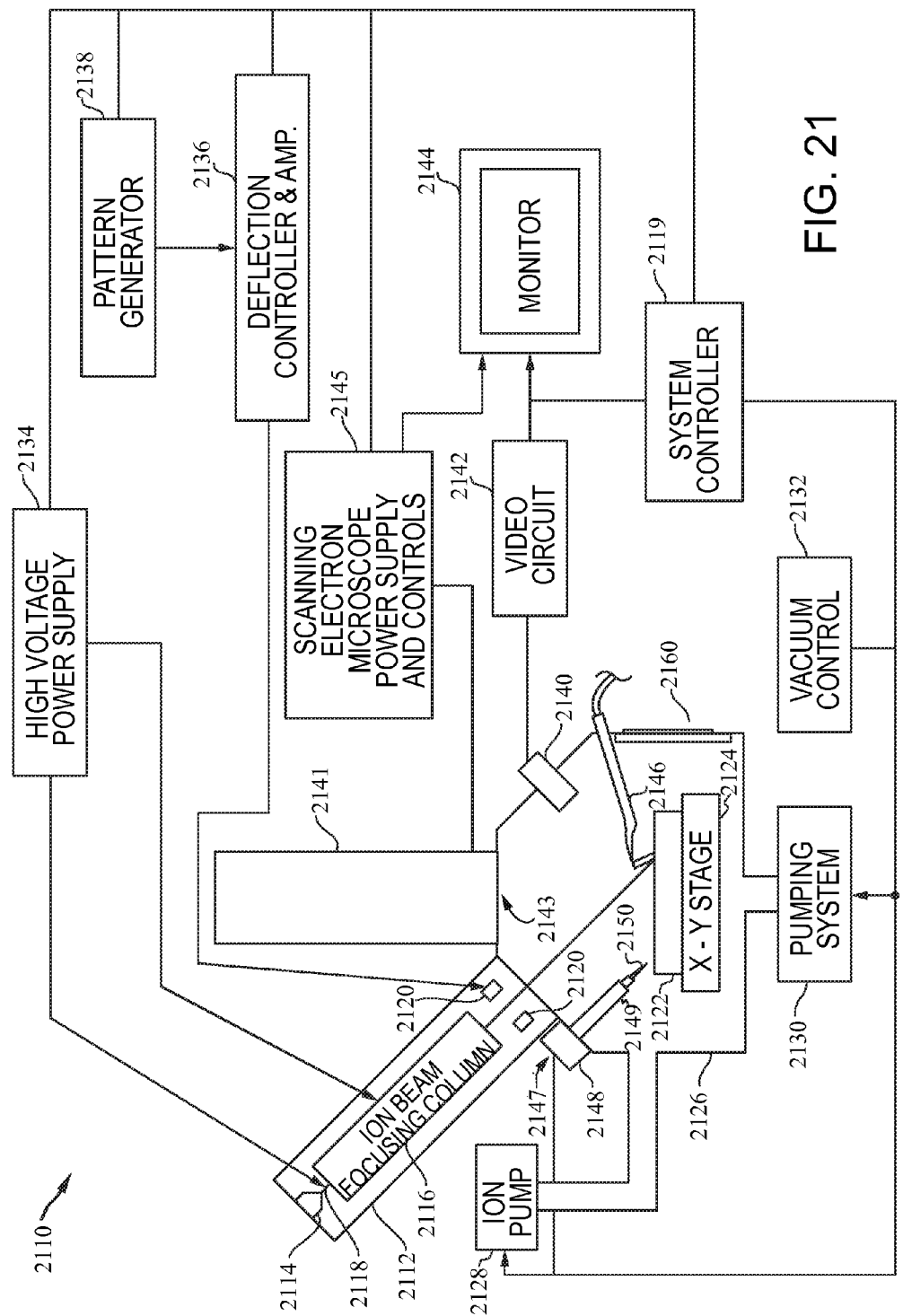
FIG. 21 shows a typical ion beam system.

FIG. 21 shows a typical ion beam system, focused ion beam (FIB) system 2110, suitable for practicing the present invention. FIB system 2110 includes an evacuated envelope having an upper neck portion 2112 within which are located a liquid metal ion source 2114 or other ion source and a focusing column 2116. Other types of ion sources, such as multicusp or other plasma sources, and other optical columns, such as shaped beam columns, could also be used, as well as electron beam and laser system.

An ion beam 2118 passes from liquid metal ion source 2114 through ion beam focusing column 2116 and between electrostatic deflection means schematically indicated at deflection plates 2120 toward work piece 2122, which comprises, for example, a semiconductor device positioned on stage 2124 within lower chamber 2126. Stage 2124 can also support one or more TEM sample holders, so that a sample can be extracted from the semiconductor device and moved to a TEM sample holder. Stage 2124 can preferably move in a horizontal plane (X and Y axes) and vertically (Z axis). Stage 2124 can also tilt approximately sixty (60) degrees and rotate about the Z axis. A system controller 2119 controls the operations of the various parts of FIB system 2110. Through system controller 2119, a user can control ion beam 2118 to be scanned in a desired manner through commands entered into a conventional user interface (not shown). Alternatively, system controller 2119 may control FIB system 2110 in accordance with programmed instructions stored in a computer readable memory, such as a RAM, ROM, or magnetic or optical disk. The memory can store instructions for carrying out the methods described above in an automated or semi-automated manner. Images from the SEM can be recognized by the software to decide when to continue processing, when to stop processing, and where to locate the beam for milling.

For example, a user can delineate a region of interest on a display screen using a pointing device, and then the system could automatically perform the steps described below to extract a sample. In some embodiments, FIB system 2110 incorporates image recognition software, such as software commercially available from Cognex Corporation, Natick, Mass., to automatically identify regions of interest, and then the system can manually or automatically extract samples in accordance with the invention. For example, the system could automatically locate similar features on semiconductor wafers including multiple devices, and take samples of those features on different (or the same) devices.

An ion pump 2128 is employed for evacuating upper neck portion 2112. The lower chamber 2126 is evacuated with turbomolecular and mechanical pumping system 2130 under the control of vacuum controller 2132. The vacuum system provides within lower chamber 2126 a vacuum of between approximately $1 \times 10^{-7}$ Torr ($1.3 \times 10^{-7}$ mbar) and $5 \times 10^{-4}$ Torr ($6.7 \times 10^{-4}$ mbar). If an etch-assisting gas, an etch-retarding gas, or a deposition precursor gas is used, the chamber background pressure may rise, typically to about $1 \times 10^{-5}$ Torr ($1.3 \times 10^{-5}$ mbar).

High voltage power supply 2134 is connected to liquid metal ion source 2114 as well as to appropriate electrodes in ion beam focusing column 2116 for forming an approximately 1 keV to 60 keV ion beam 2118 and directing the same toward a sample. Deflection controller and amplifier 2136, operated in accordance with a prescribed pattern provided by pattern generator 2138, is coupled to deflection plates 2120 whereby ion beam 2118 may be controlled manually or automatically to trace out a corresponding pattern on the upper surface of work piece 2122. In some systems the deflection plates are placed before the final lens, as is well known in the art. Beam blanking electrodes (no shown) within ion beam focusing column 2116 cause ion beam 2118 to impact onto blanking aperture (not shown) instead of target 2122 when a blanking controller (not shown) applies a blanking voltage to the blanking electrode.

The liquid metal ion source 2114 typically provides a metal ion beam of gallium. The source typically is capable of being focused into a sub one-tenth micrometer wide beam at work piece 2122 for either modifying the work piece 2122 by ion milling, enhanced etch, material deposition, or for the purpose of imaging the work piece 2122. A charged particle detector 2140, such as an Everhart Thornley or multi-channel plate, used for detecting secondary ion or electron emission is connected to a video circuit 2142 that supplies drive signals to video monitor 2144 and receiving deflection signals from controller 2119.

The location of charged particle detector 2140 within lower chamber 2126 can vary in different embodiments. For example, a charged particle detector 2140 can be coaxial with the ion beam and include a hole for allowing the ion beam to pass. In other embodiments, secondary particles can be collected through a final lens and then diverted off axis for collection. A scanning electron microscope (SEM) 2141, along with its power supply and controls 2145, are optionally provided with the FIB system 2110.

A gas delivery system 2146 extends into lower chamber 2126 for introducing and directing a gaseous vapor toward work piece 2122. U.S. Pat. No. 5,851,413 to Casella et al. for "Gas Delivery Systems for Particle Beam Processing," assigned to the assignee of the present invention, describes a suitable gas delivery system 2146. Another gas delivery system is described in U.S. Pat. No. 5,435,850 to Rasmussen for a "Gas Injection System," also assigned to the assignee of the present invention. For example, iodine can be delivered to enhance etching, or a metal organic compound can be delivered to deposit a metal.

A micromanipulator 2147, such as the AutoProbe 200® from Omniprobe, Inc., Dallas, Tex., or the Model MM3A from Kleindiek Nanotechnik, Reutlingen, Germany, can precisely move objects within the vacuum chamber. Micromanipulator 2147 may comprise precision electric motors 2148 positioned outside the vacuum chamber to provide X, Y, Z, and theta control of a portion 2149 positioned within the vacuum chamber. The micromanipulator 2147 can be fitted with different end effectors for manipulating small objects. In the embodiments described below, the end effector is a thin probe 2150. The thin probe 2150 may be electrically connected to system controller 2119 to apply an electric charge to the probe 2150 to control the attraction between a sample and the probe.

A door 2160 is opened for inserting work piece 2122 onto X-Y stage 2124, which may be heated or cooled, and also for servicing an internal gas supply reservoir, if one is used. The door is interlocked so that it cannot be opened if the system is under vacuum. The high voltage power supply provides an appropriate acceleration voltage to electrodes in ion beam focusing column focusing 2116 for energizing and focusing ion beam 2118. When it strikes work piece 2122, material is sputtered, that is physically ejected, from the sample. Alternatively, ion beam 2118 can decompose a precursor gas to deposit a material. Focused ion beam systems are commercially available, for example, from FEI Company, Hillsboro, Oreg., the assignee of the present application. While an example of suitable hardware is provided above, the invention is not limited to being implemented in any particular type of hardware.

Although the description of the present invention above is mainly directed at a method of producing TEM lamella, the method robust, repeatable and therefore suitable for automation, it should be recognized that an apparatus performing the operation of this method would further be within the scope of the present invention. Further, it should be recognized that embodiments of the present invention can be implemented via computer hardware or software, or a combination of both. The methods can be implemented in computer programs using standard programming techniques—including a computer-readable storage medium configured with a computer program, where the storage medium so configured causes a computer to operate in a specific and predefined manner—according to the methods and figures described in this Specification. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits programmed for that purpose.

Further, methodologies may be implemented in any type of computing platform, including but not limited to, personal computers, mini-computers, main-frames, workstations, networked or distributed computing environments, computer platforms separate, integral to, or in communication with charged particle tools or other imaging devices, and the like. Aspects of the present invention may be implemented in machine readable code stored on a storage medium or device, whether removable or integral to the computing platform, such as a hard disc, optical read and/or write storage mediums, RAM, ROM, and the like, so that it is readable by a programmable computer, for configuring and operating the computer when the storage media or device is read by the computer to perform the procedures described herein. Moreover, machine-readable code, or portions thereof, may be transmitted over a wired or wireless network. The invention described herein includes these and other various types of computer-readable storage media when such media contain instructions or programs for implementing the steps described above in conjunction with a microprocessor or other data processor. The invention also includes the computer itself when programmed according to the methods and techniques described herein.

Computer programs can be applied to input data to perform the functions described herein and thereby transform the input data to generate output data. The output information is applied to one or more output devices such as a display monitor. In preferred embodiments of the present invention, the transformed data represents physical and tangible objects, including producing a particular visual depiction of the physical and tangible objects on a display.

Preferred embodiments of the present invention also make use of a particle beam apparatus, such as a FIB or SEM, in order to image a sample using a beam of particles. Such particles used to image a sample inherently interact with the sample resulting in some degree of physical transformation. Further, throughout the present specification, discussions utilizing terms such as "calculating," "determining," "measuring," "generating," "detecting," "forming," or the like, also refer to the action and processes of a computer system, or similar electronic device, that manipulates and transforms data represented as physical quantities within the computer system into other data similarly represented as physical quantities within the computer system or other information storage, transmission or display devices.

The invention has broad applicability and can provide many benefits as described and shown in the examples above. The embodiments will vary greatly depending upon the specific application, and not every embodiment will provide all of the benefits and meet all of the objectives that are achievable by the invention. Particle beam systems suitable for carrying out the present invention are commercially available, for example, from FEI Company, the assignee of the present application. However, even though much of the previous description is directed toward the use of FIB milling and imaging, the beam used to process the desired samples could comprise, for example, an electron beam, a laser beam, or a focused or shaped ion beam, for example, from a liquid metal ion source or a plasma ion source, or any other charged particle beam. Further, although much of the previous description is directed at particle beam systems, the invention could be applied to any suitable sample imaging system employing a moveable sample stage to navigate to the location of a sample feature.

Although much of the previous description is directed at semiconductor wafers, the invention could be applied to any suitable substrate or surface. Further, whenever the terms "automatic," "automated," or similar terms are used herein, those terms will be understood to include manual initiation of the automatic or automated process or step. Whenever a scan or image is being processed automatically using computer processing, it should be understood that the raw image data can be processed without ever generating an actual viewable image. The term "image" is used in a broad sense to include not only a displayed image showing the appearance of the surface, but also to include any collection of information characterizing the multiple points on or below a surface. For example, a collection of data corresponding to the secondary electrons collected when a particle beam is at different point on a surface is a type of "image," even if the data is not displayed. Collecting information about points on the sample or work piece is "imaging."

In the following discussion and in the claims, the terms "including" and "comprising" are used in an open-ended fashion, and thus should be interpreted to mean "including, but not limited to . . . ." The term "integrated circuit" refers to a set of electronic components and their interconnections (internal electrical circuit elements, collectively) that are patterned on the surface of a microchip. The term "semiconductor device" refers generically to an integrated circuit (IC), which may be integral to a semiconductor wafer, separated from a wafer, or packaged for use on a circuit board. The term "FIB" or "focused ion beam" is used herein to refer to any collimated ion beam, including a beam focused by ion optics and shaped ion beams.

When the positional error or accuracy of the system stage or of beam placement or navigation is discussed herein, the terms ±100 nm (or ±30 nm or ±X nm) mean that the beam can be directed at a location on the sample within a maximum error of 100 nm (or 30 nm or x nm). The terms "accuracy of ±X nm" or "positioning accuracy of X nm or better" means that the accuracy is at least X nm and includes all smaller values. The term "accuracy of X nm or greater" means that the accuracy is at best X nm and includes all larger values.

To the extent that any term is not specially defined in this specification, the intent is that the term is to be given its plain and ordinary meaning. The accompanying drawings are intended to aid in understanding the present invention and, unless otherwise indicated, are not drawn to scale.

Although the present invention and its advantages have been described in detail, it should be understood that various changes, substitutions, and alterations can be made to the embodiments described herein without departing from the spirit and scope of the invention as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim as follows:

1. A method of forming a lamella having an observation face for transmission electron microscope observation of a feature of interest in the observation face, comprising:
    directing a charged particle beam toward a work piece in the vacuum chamber of a charged particle beam system to induce deposition from a precursor gas of a protective layer above the feature of interest, the ratio of the sputtering rate of the work piece and the sputtering rate of the protective layer being within a ratio of 1.5 to 1 and a ratio of 1:1, the work piece comprising silicon;
    directing a focused ion beam toward the sample to mill one or more fiducials near the feature of interest;
    directing the focused ion beam to mill cavities on both sides of the region of interest to form a lamella;
    from each side of the lamella, directing the focused ion beam to mill progressively closer to the observation face from the cavity, successively milling to remove less material from the lamella as the beam approaches the region of interest to provide a bottom surface of the lamella that slopes away from the observation face, the ions in the focused ion beam having a first landing energy;
    after milling progressively closer to the observation face from the cavity, milling to remove material separating the cavities to leave tabs supporting the cavity;
    after milling to remove material separating the cavities, directing an ion beam toward the observation face, the ion beam having a second landing energy, lower than the first landing energy.

2. The method of claim 1 in which the first landing energy is greater than 20,000 eV and the second landing energy is less than 15,000 eV.

3. The method of claim 2 in which the first landing energy is greater than 25,000 eV and the second landing energy is less than 10,000 eV.

4. The method of claim 2 in which the first landing energy is greater than 28,000 eV and the second landing energy is less than 6,000 eV.

5. The method of claim 1 further comprising separating the lamella milling from the sample inside the vacuum chamber.

6. The method of claim 1 further comprising separating the lamella milling from the sample outside the vacuum chamber.

7. The method of claim 1 in which directing a focused ion beam to mill progressively closer to the observation face from the cavity, successively milling to remove less material from the lamella as the beam approaches the region of interest to provide a bottom surface of the lamella that slopes away from the observation face includes thinning the lamella to less than 100 nm thickness.

8. The method of claim 7 in which the steps are performed automatically without human intervention.

9. The method of claim 7 in which the lamella is thinned to less than 70 nm.

10. The method of claim 7 in which the lamella is thinned to less than 50 nm.

11. The method of claim 1 in which directing a focused ion beam to mill progressively closer to the observation face from the cavity includes determining a beam position using the fiducial prior to the final milling.

12. The method of claim 1 further comprising after milling progressively closer to the observation face from the cavity directing a defocused ion beam to toward the observation face, the energy of the ions in the defocused ion beam less than the energy of the ions used to form the cavities.

13. The method of claim 12 in which directing a defocused ion beam to toward the observation face includes successively directing the defocused ion beam toward the observation face, with a delay between successive applications of the beam.

14. The method of claim 1 further comprising viewing the lamella with a scanning electron microscope to determine its thickness.

15. The method of claim 14 further comprising milling a cross section in the lamella and viewing the cross section with the scanning electron microscope before the lamella is separated from the work piece.

16. The method of claim 1 in which directing a focused ion beam toward the sample to mill one or more fiducials near the feature of interest includes milling two fiducials, one on either side of the lamella to be formed, the fiducials aligned with the center of the lamella to be formed.

17. The method of claim 1 in which directing a focused ion beam toward the sample to mill one or more fiducials near the feature of interest includes milling two fiducials, one on either side of the lamella to be formed, the fiducials offset from the center of the lamella to be formed.

18. The method of claim 1 in which directing a focused ion beam to mill progressively closer to the observation face from the cavity includes determining a beam drift at least once during milling and correcting the position of the beam to compensated for the drift.

19. The method of claim 1 in which the protective layer comprises: tungsten or carbon.

20. The method of claim 1 in which directing the focused ion beam to mill progressively closer to the observation face from the cavity further comprises directed the focused ion beam at a grazing angle with respect to the observation face, the grazing angle being no greater than 40 degrees with respect to the observation face.

* * * * *